US010196597B2

(12) United States Patent
Assulin (10) Patent No.: US 10,196,597 B2
(45) Date of Patent: Feb. 5, 2019

(54) BIOMASS CARRIER AND A METHOD OF MANUFACTURING THEREOF

(71) Applicant: Aqwise-Wise Water Technologies Ltd., Herzliya (IL)

(72) Inventor: Nir Assulin, Kiryat Tivon (IL)

(73) Assignee: AQWISE-WISE WATER TECHNOLOGIES LTD, Herzliya (IL)

(*) Notice: Subject to any disclaimer, the term of this patent is extended or adjusted under 35 U.S.C. 154(b) by 142 days.

(21) Appl. No.: 15/124,933

(22) PCT Filed: Mar. 11, 2015

(86) PCT No.: PCT/IL2015/050255
§ 371 (c)(1),
(2) Date: Sep. 9, 2016

(87) PCT Pub. No.: WO2015/136535
PCT Pub. Date: Sep. 17, 2015

(65) Prior Publication Data
US 2017/0015969 A1 Jan. 19, 2017

Related U.S. Application Data

(60) Provisional application No. 61/951,134, filed on Mar. 11, 2014.

(51) Int. Cl.
*B01J 19/30* (2006.01)
*C02F 3/10* (2006.01)
(Continued)

(52) U.S. Cl.
CPC .............. *C12M 25/14* (2013.01); *B01J 19/30* (2013.01); *B29C 47/0014* (2013.01);
(Continued)

(58) Field of Classification Search
CPC ........ C12M 25/14; C12M 25/20; B01J 19/30; B29C 47/30; B29C 47/065; B29C 47/26;
(Continued)

(56) References Cited

U.S. PATENT DOCUMENTS 2,919,467 A  1/1960  Mercer
3,123,512 A  3/1964  Mercer
(Continued)

FOREIGN PATENT DOCUMENTS

CN    2306990 Y    2/1999
CN   101553436 A  10/2009
(Continued)

OTHER PUBLICATIONS

Aqwise-Wise Water Technologies Ltd. "The Agar Trademark Technology for Biological Wastewater Treatment for Biological Wastewater Treatment." Nov. 11, 2007.
(Continued)

*Primary Examiner* — Claire A Norris
(74) *Attorney, Agent, or Firm* — Pearl Cohen Zedek Latzer Baratz LLP (57) ABSTRACT

A compressible biomass carrier for use in fluid treatment systems is disclosed. The biomass carrier includes an extruded circumferential mesh-like structure and elongated elements positioned in a space confined by the circumferential mesh-like structure and at least some of the elongated elements are joined to an inner portion of the mesh-like structure.

23 Claims, 5 Drawing Sheets

(51) Int. Cl.
    *C12M 1/12*      (2006.01)
    *B29C 47/00*      (2006.01)
    *B29C 47/02*      (2006.01)
    *B29C 47/04*      (2006.01)
    *B29C 47/12*      (2006.01)
    *B29C 47/24*      (2006.01)
    *B29C 47/28*      (2006.01)
    *B29C 47/86*      (2006.01)
    *B29C 47/92*      (2006.01)
    *B29C 47/06*      (2006.01)
    *B29L 28/00*      (2006.01)

(52) U.S. Cl.
CPC ...... *B29C 47/0064* (2013.01); *B29C 47/0066* (2013.01); *B29C 47/026* (2013.01); *B29C 47/028* (2013.01); *B29C 47/04* (2013.01); *B29C 47/067* (2013.01); *B29C 47/122* (2013.01); *B29C 47/24* (2013.01); *B29C 47/28* (2013.01); *B29C 47/864* (2013.01); *B29C 47/92* (2013.01); *C02F 3/108* (2013.01); *C02F 3/109* (2013.01); *C12M 25/20* (2013.01); *B01J 2219/30223* (2013.01); *B01J 2219/30242* (2013.01); *B01J 2219/30466* (2013.01); *B29C 2947/92704* (2013.01); *B29L 2028/00* (2013.01); *Y02W 10/15* (2015.05)

(58) Field of Classification Search
CPC . B29C 47/02; B29C 47/0014; B29C 47/0064; B29C 47/0066; B29C 47/026; B29C 47/028; B29C 47/04; B29C 47/067; B29C 47/122; B29C 47/24; B29C 47/28; B29C 47/864; B29C 47/92; C02F 3/108; C02F 3/109
USPC ........................... 210/150, 615; 264/DIG. 81
See application file for complete search history.

(56) References Cited

U.S. PATENT DOCUMENTS

| | | | |
|---|---|---|---|
| 3,239,884 A | | 3/1966 | Seidel |
| 3,538,545 A | | 11/1970 | Smith |
| 3,553,341 A | * | 1/1971 | Hureau ................ B29C 47/02 174/107 |
| 3,620,883 A | * | 11/1971 | Nalle, Jr. ............ B29C 47/0033 156/167 |
| 3,749,535 A | | 7/1973 | Gaffney |
| 3,767,353 A | | 10/1973 | Gaffney |
| 3,874,834 A | | 4/1975 | Arechavaleta |
| 4,656,075 A | | 4/1987 | Mudge |
| 2003/0127378 A1 | | 7/2003 | Shechter |
| 2006/0270024 A1 | * | 11/2006 | Uphoff .................... C02F 3/06 435/292.1 |
| 2011/0027870 A1 | * | 2/2011 | Assulin .................. B01J 19/30 435/266 |
| 2012/0055870 A1 | * | 3/2012 | Pajuniemi ............ B01J 10/002 210/615 |
| 2013/0300024 A1 | | 11/2013 | Morris |

FOREIGN PATENT DOCUMENTS

| | | |
|---|---|---|
| CN | 202 829 701 | 3/2013 |
| DE | 69303181 | 10/1996 |
| GB | 1235322 | 6/1971 |
| GB | 2156263 | 10/1985 |
| JP | H111682 | 1/1999 |
| WO | WO 2008/066244 | 6/2008 |

OTHER PUBLICATIONS

International Search Report for International Appl. No. PCT/IL2015/050255 dated May 28, 2015.
Office Action dated Apr. 20, 2018 for U.S. Appl. No. 15/124,391.
Office Action dated Sep. 7, 2018 for U.S. Appl. No. 15/124,391.

* cited by examiner

FIG. 4

BIOMASS CARRIER AND A METHOD OF MANUFACTURING THEREOF

CROSS-REFERENCE TO RELATED APPLICATIONS

This application is a National Phase Application of PCT International Application No. PCT/IL2015/050255, International Filing Date Mar. 11, 2015, claiming the benefit of U.S. Provisional Patent Application No. 61/951,134, filed Mar. 11, 2014 which are hereby incorporated in their entirety.

BACKGROUND

Various biological fluid treatment processes are based on disintegration of unwanted bio-degradable substances from the fluid by microorganisms growing in the fluid. Such biological fluid treatment processes may utilize biomass carriers for growing the microorganism. For example, the biomass carriers in liquid treatment are usually relatively small elements having a density close to water density so as to be kept suspended in the water. The larger the surface area of a biomass carrier available for the development of microorganisms per volume of the biomass carrier the more efficient is the removal of the bio-degradable substances. Consequently, biomass carriers have usually a complex design with multiple pores. The carrier's manufacturing cost depends mostly on the raw material quantity required to support the high surface area. Moreover, the carrier structure is very volumetric enclosing high void volume, influencing the shipment costs.

SUMMARY

Some embodiments of the invention are directed to compressible biomass carriers for use in a fluid treatment system. The biomass carrier includes an extruded circumferential mesh-like structure and elongated elements positioned in a space confined by the circumferential mesh-like structure, at least some of which are joined to an inner portion of the mesh-like structure.

Some embodiments of the invention are directed to a method of manufacturing a biomass carrier. The method may include feeding solid elongated elements comprising polymeric material into a protective sleeve located inside a hollow die during extrusion of a polymeric mesh-like structure, extruding the mesh-like structure from the die while directing the elongated elements to exit the die via an opening in the die and joining the elongated elements to an internal surface of the mesh-like structure.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently.

Embodiments of the invention are directed to biomass carriers for biological fluid treatments, such as liquid and/or gas treatment processes. Biomass carriers are elements having complex shapes having a relatively large surface area per volume ratio. In some embodiments the biomass carrier is a compressible object that includes an extruded circumferential mesh-like structure and elongated elements positioned in a space confined by the circumferential mesh-like structure such that at least some of the elongated elements are joined or affixed to an inner portion of the mesh-like structure.

For example, in some embodiments, the effective surface area measured for a plurality of biomass carriers may be 100-2000 square meter ($m^2$) per cubic meter ($m^3$) of bulk carrier volume. The biomass carriers may be plastic elements having a specific gravity or density close to water density. A biomass carrier, according to embodiments of the invention may be self-supported element capable of floating in liquids. For example, the density of the biomass carriers varies and may be slightly lower or slightly higher than water density The length of the biomass carrier may be in the range of around 5 mm to around 50 mm. For example, exemplary biomass carriers according to embodiments of the invention may have a largest dimension which does not exceed 50 mm. A carrier, according to embodiments of the invention, may include an extruded circumferential mesh-like structure that encompasses a plurality of substantially elongated elements also referred herein as strips.

The strips may be positioned in a space confined by the circumferential mesh-like structure, such that at least some of the strips are joined, affixed or connected to an inner portion of the mesh-like structure. For example, the stripes may be fused, connected, welded, glued or adhered to the mesh-like structure by any suitable method. In connection to embodiments of the invention, the terms "jointed" and "connected" include any suitable method for connecting or joining the strips and the inner structure of the mesh-like structure including but not limited to fused, welded, glued and adhered. The thickness of the mesh may be in the range of around 50-1000 μm. For example, the thickness of the mesh may be in the range of around: below 1000 μm, below 500 μm, below 300 μm, below 200 μm or below 100 μm. The thickness of the elongated elements may be in the range of around 10-500 μm. For example, the thickness of the elongated elements may be in the range of around: below 400 μm, below 300 μm, below 200 μm, below 100 μm or below 50 μm. Biomass carriers according to some embodiments of the invention may have a density in the range of around 0.8-1.2 gram/cm$^3$.

Biomass carriers according to embodiments of the invention may be included in a system for biological fluid treatments. The biomass carriers may be introduced to at least one reactor of the system together with the fluid to be treated. A biomass (e.g., microorganisms) growing on the biomass carriers in the reactor may cause the disintegration of bio-degradable substances included in the fluid. In some embodiments, the biomass carriers may be introduced into two or more reactors of the system. Biomass carriers may be inserted to the liquid treatment reactors at a fill ratio of 20-70 percent of the total fluid volume.

In some embodiments, the carriers may be manufactured by a combined extrusion method, in which a partial structure is manufactured by extrusion and simultaneously other portions of the structure, namely, the elongated elements or strips are connected to the extruded mesh structure thus forming a combined structure. During manufacturing, molten polymer (i.e., plastic) may be inserted into an extruder, for example, a mesh or net extruder to form the extruded structure while polymer strips that would form the elongated elements of the carrier may be inserted to an inner tube in a die of the mesh extruder. The elongated elements may be kept in a solid state and may further be arranged at a desired arrangement. The elongated elements may exit the die from the same side as the circumferential mesh-like structure and may be joined to the extruded circumferential mesh-like structure as the mesh, still in liquid (melt) or glassy condition, exits the die.

Figure 1A:
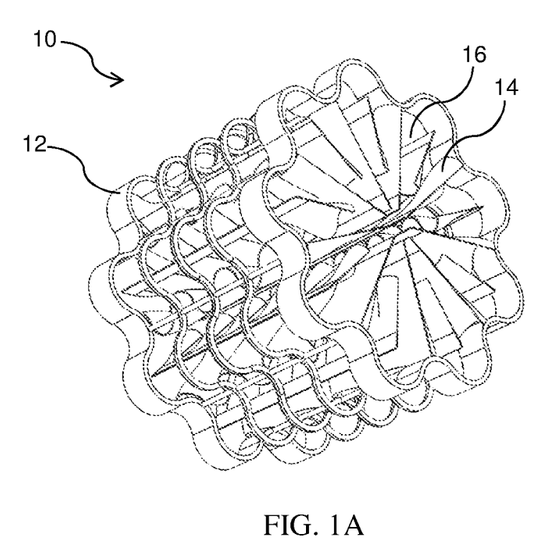
FIG. 1A is an illustration of an exemplary biomass carrier according to some embodiments of the invention.

Reference is made to FIG. 1A illustrating an exemplary biomass carrier according to some embodiments of the invention. A biomass carrier 10 may include an extruded circumferential mesh-like structure 12 and two or more elongated elements or strips 14 positioned in a space 16 confined by the circumferential mesh-like structure. At least some of elongated elements 14 may be joined to an inner area of mesh-like structure 12. In some embodiments, each of strips 14 may be joined to the inner area of mesh-like structure 12. In some embodiments some of the strips 14 may be joined to each other. In the exemplary embodiment of FIG. 1A eighteen (18) strips are shown. It should be understood, however, to a person skilled in the art that any other number of strips is within the scope of the invention. Further, it should be understood, to a person skilled in the art that many other configurations and arrangements of the strips are within the scope of the invention.

In some embodiments, the biomass carriers may be configured to be compressed under pressure for example during packaging and may substantially resume their original shape when the pressure is removed, for example when inserted into liquid. Upon applying pressure biomass carrier 10 may collapse and diminish its confined volume. According to embodiments of invention, carrier 10 may be configured to be compressed, for example, below at least 70% of its original confined volume. According to embodiments of invention, carrier 10 may be configured to be compressed, for example, below at least 50% of its original confined volume. When packed for shipment or delivery, a plurality of biomass carriers 10 included in a package may be compressed by applying an external force such that the volume that the plurality of biomass carriers 10 occupy in the package may be reduced to below at least 70%, 50%, 40% or 30% of the original volume occupied by the plurality of biomass carriers 10 prior to the application of the external force. The compression ratio of the biomass carriers may be between around 1:1.4 to 1:3. For example, one cubic meter of biomass carriers may be compressed to occupy a volume of 0.7-0.3 cubic meter.

Extruded circumferential mesh-like structure 12 may form the outer wall(s) of carrier 10 defining the confined space 16. The extruded circumferential mesh-like structure may include a plastic mesh having a plurality of holes. The holes may have any shape, for example rectangle, circle, rhombus or the like. Extruded circumferential mesh-like structure 12 may have a thickness of less than 1000 micron, namely, the circumferential wall of structure 12 may have a thickness of less than 1000 micron. In some embodiments, Extruded circumferential mesh-like structure 12 may have a thickness of less than 250 micron. An exemplary mesh may have a thickness of 50-500 micron, a length of 5-50 mm and an outer dimension (e.g., a diameter, a length, a diagonal, or the like) of 5 mm-50 mm. Extruded circumferential mesh-like structure 12 may be extruded from various polymers (i.e., plastics) for example, high density polyethylene (HDPE), polyethylene terephthalate (PET), low density polyethylene (LDPE) or polypropylene (PP) and others.

Figure 1B:
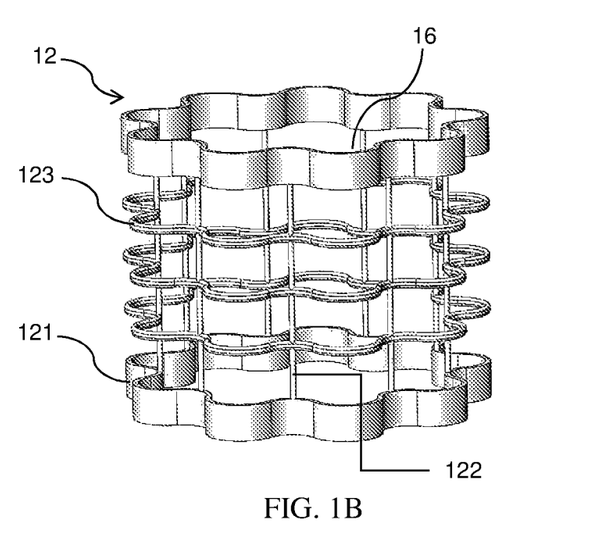
FIG. 1B is an illustration of exemplary extruded circumferential mesh-like structure of the exemplary biomass carrier of FIG. 1A according to some embodiments of the invention.
Figure 2A:
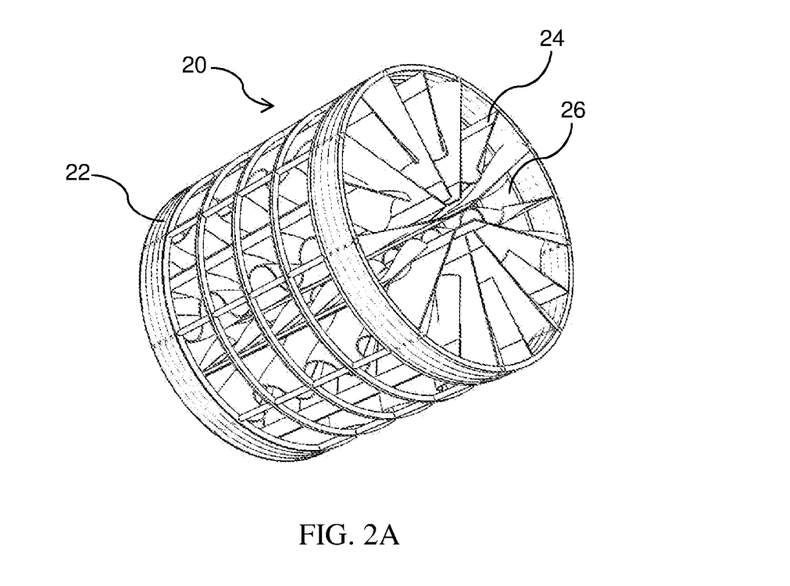
FIG. 2A is an illustration of an exemplary biomass carrier according to some embodiments of the invention.

An exemplary extruded circumferential mesh-like structure 12 is illustrated in FIG. 1B. Exemplary mesh 12 may have a wavy shape with rectangular holes. Exemplary mesh 12 may include two end rings 121 and a plurality of substantially vertical or diagonal cords 122. In some embodiments, mesh 12 may further include one or more inner rings 123. For example, mesh 12 may include two end rings 121 and 7 vertical cords 122, or two end rings 121, 3 inner rings 123 and 9 cord 122, as illustrated. Exemplary meshes according to the invention may include around 0-25 inner rings 123 and around 3-80 cords 122. In some embodiments, mesh 12 may include a plurality of extruded lines (or vertical/diagonal cord) crossing each other to produce rhombus mesh. In some embodiments, the mesh may have a cylindrical shape as illustrated in FIGS. 2A-2B.

Figure 2B:
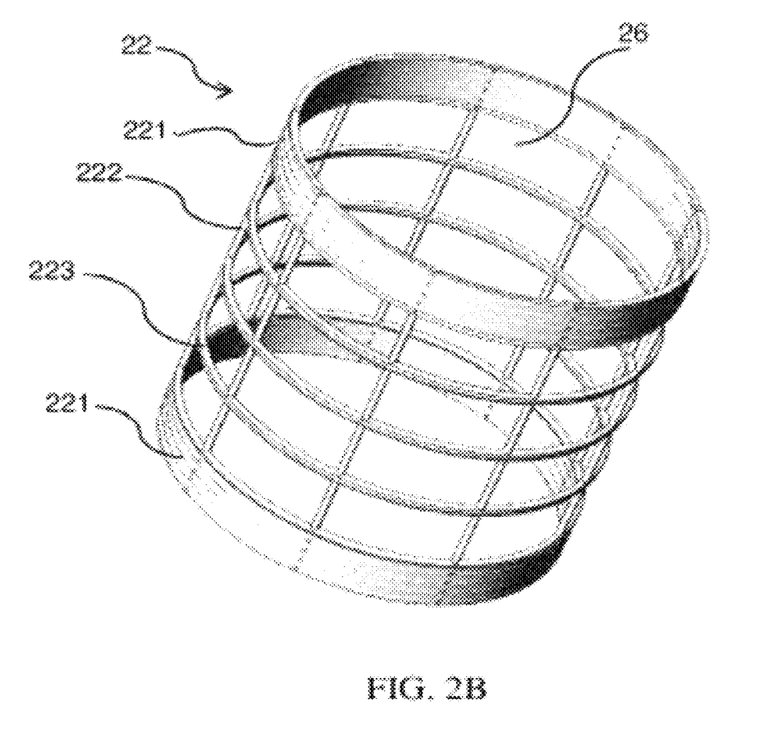
FIG. 2B is an illustration of an exemplary extruded circumferential mesh-like structure of the exemplary biomass carrier of FIG. 2A according to some embodiments of the invention.

As it will be understood by a person skilled in the art, that the invention is not limited to the exemplary meshes illustrated in FIGS. 1B and 2B having an axial symmetry and rectangular holes. The invention may include any plastic mesh that may be manufactured by extrusion having holes in any shape and number.

Elongated elements 14 may be plastic strips made from various polymers (i.e., plastics) for example, high density polyethylene (HDPE), polyethylene terephthalate (PET), low density polyethylene (LDPE) or polypropylene (PP). Each elongated element 14 may have a thickness of less than 500 micron. An exemplary elongated element 14 may have the thickness of 10-250 microns and the width of 2.5 mm-10 mm. Elongated elements 14 may have the same length as extruded circumferential mesh-like structure 12, for example 5 mm-50 mm. Elongated elements 14 may be flat or wavy, straight or curved or a combination thereof, or may take any shape that may increase the attachment surface of biomass carrier 10. The surface of elongated elements 14 may be smooth or rough and/or may be punched with small holes. At least some of elongated elements 14 may be joined (e.g., welded, glued, or the like) to mesh 12 from at least one side, as illustrated. Elongated element 14 may be coated with an active coating, for example, a coating configured to enhance the growth of the biomass on the biomass carrier, a coating configured to absorb waste material or the like.

Figure 1C:
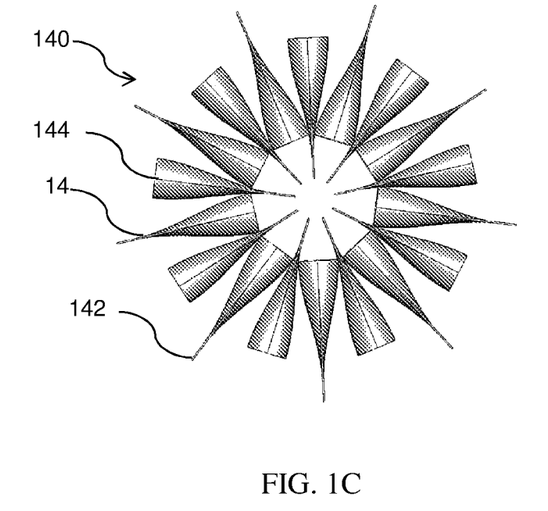
FIG. 1C is an illustration of exemplary arrangement of elongated elements in the exemplary biomass carrier of FIG. 1A according to some embodiments of the invention.

In some embodiments, elongated elements 14 may be located inside space 16 in a pre-designed arrangement optimally designed to increase the active surface area to biomass carrier 10. Alternatively, elongated elements 14 may be located inside space 16 in an arbitrary arrangement. An exemplary arrangement 140 of elements 14 is illustrated in FIG. 1C. Exemplary elongated elements 14 may have a straight portion and/or a curved wing-like portion and may be arranged in a flower-like arrangement where eight (8) wing-like elongated elements 142 are located such that a straight portion of the fin is facing the outer periphery of arrangement 140 and eight (8) wing-like elongated elements 144 are located such that the straight portion of the fin is facing the inner portion of arrangement 140. In some embodiments, arrangement 140 may be joined (e.g., welded) to mesh 12 along the 8 straight ends of elongated elements 142 (as illustrated in FIG. 1A). Each of elongated elements 144 may be joined (e.g., welded, glued, or the like) to a neighboring elongated element 142.

Biomass carrier 10 may be manufactured in a single process. Molten polymer may be inserted into an extruder and a die configured to extrude a mesh. Two or more inner plastic elongated elements 14 may be inserted along an open tube located along the middle axis of the die, such that the desired (either arbitrary or pre-designed) arrangement of the elongated elements is kept (e.g., arrangement 140). The elongated elements may be connected to the extruded circumferential mesh-like structure when the mesh exits the die of the extruder. A method for producing biomass carriers according to some embodiments of the invention is disclosed below and in FIG. 3.

Reference is made to FIG. 2A, which illustrates an exemplary biomass carrier 20 according to some embodiments of the invention. Biomass carrier 20 may include an extruded circumferential mesh-like structure 22 and two or more elongated elements 24 positioned in a space 26 confined by the circumferential mesh-like structure, such that at least some of the elongated elements are joined to an inner portion of the mesh-like structure. In some embodiments, biomass carrier 20 may be collapsible and configured to be compressed during packing to at least 70% of its original volume. For example, biomass carrier 20 may have a compression ratio of in the range of around 1:1.4 to 1:3.

Extruded circumferential mesh-like structure 22 may form the outer wall(s) of confined space 26 of carrier 20. Mesh 20 may include a plastic mesh having a plurality of holes. The holes may have any shape, for example rectangle, circle, rhombus or the like. Extruded circumferential mesh-like structure 22 may have a thickness (of the wall(s)) of less than 1000 micron or even less than 250 micron. An exemplary mesh 22 may have a thickness of around 20-150 micron, a length of around 5 mm-50 mm and an outer dimension (e.g., a diameter, a side, a diagonal, or the like) of around 5 mm-50 mm. Extruded circumferential mesh-like structure 22 may be extruded from various polymers (i.e., plastics) for example, High-density polyethylene (HDPE), Polyethylene terephthalate (PET), Low-density polyethylene (LDPE), polypropylene (PP) and the like.

An exemplary extruded circumferential mesh-like structure 22 is illustrated in FIG. 2B. Exemplary mesh 22 may have a cylindrical shape with rectangular holes. Exemplary mesh 22 may include two side-rings 221 and a plurality of threads 222. In some embodiments, mesh 22 may further include one or more inner rings 223. Exemplary meshes according to the invention may include 0-18 inner rings 223 and 3-80 threads 222. Elongated elements 24 may be substantially the same as elongated elements 14 discussed with respect to FIG. 2A. Elongated elements 14 may be located inside space 26 and arranged in a pre-designed desired arrangement, as disclosed with respect to arrangement 140 or in arbitrary arrangement. The desired arrangement may be designed to increase the attachment surface of the biomass in biomass carrier 20. The desired arrangement of elongated elements 24 may include two or more elongated elements 24 (e.g., 6-80 elongated elements 24) and may be encompass by extruded circumferential mesh-like structure 22. At least some of elongated elements 24 may be joined (e.g., welded, glued, or the like) to mesh 22. Biomass carrier 20 may be manufactured in a single process, in a similar way to biomass carrier 10.

Biomass carriers according to embodiments of the invention, for example, carriers 10 and 20, may be coated. The coating may be applied to at least a portion of the carrier, for example, the coating may be applied to the circumferential mesh-like structure (e.g., structures 12 and 22) and/or may be applied to at least some of the elongated elements (e.g., elements 14 and 24) or any other portion of the biomass carriers. The coating may include any material that includes an active component, for example, a component that enhances and encourage the growth of the biomass on the biomass carrier or a component that absorb waste material or any catalytic compound. Non-exhaustive examples of suitable active components may include active carbon, carbon nanotubes, or other surface reactive materials for example titanium oxide. The coating may be added following the extrusion process. Alternatively, the coating may be applied onto the elongated elements prior to the extrusion process. The application of the coating material may be carried out using any method of coating known in the art, such as for example, spattering, spraying, immersion, etc.

Figure 4:
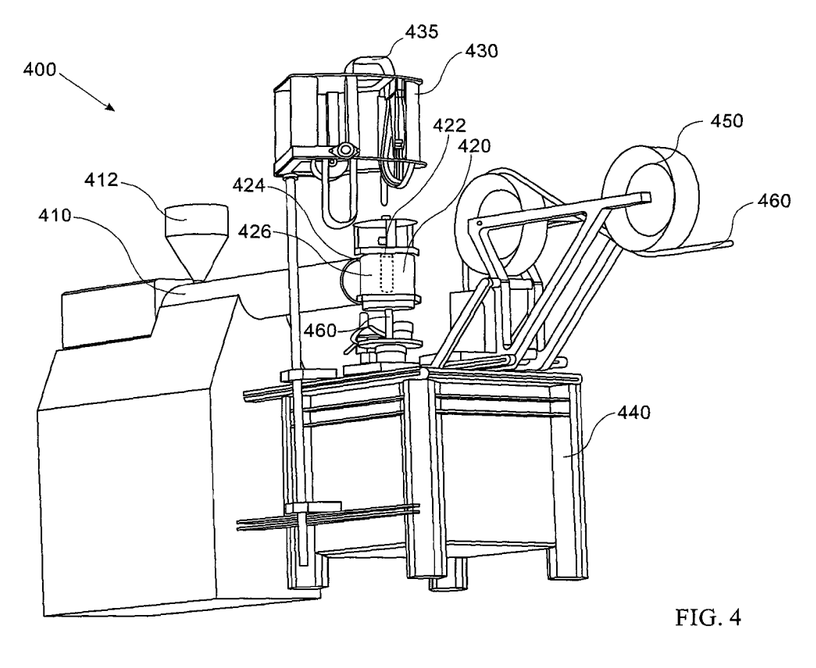
FIG. 4 is an illustration of an exemplary apparatus for making biomass carriers according to some embodiments of the invention.

In some embodiments, the active material may be added and mixed with the flowing (e.g., molten) polymer inside extruder body 110. The active material may be introduced together with the polymeric material via inlet 112, for example, in a form of a powder. The active material may be mixed with the plowing polymeric material prior to the extrusion of the mesh-like structure. The active material particles may be embedded in the polymeric material of the extruded mesh-like structure to form a composite material. In some embodiments, an extruded mesh-like structure that includes the composite material may be affixed or joined with elongated elements that were at least partially coated with an active material. The active material added to the extruded flowing polymer may be similar or different from the active material applied as coating to at least a portion of the elongated elements.

Figure 3:
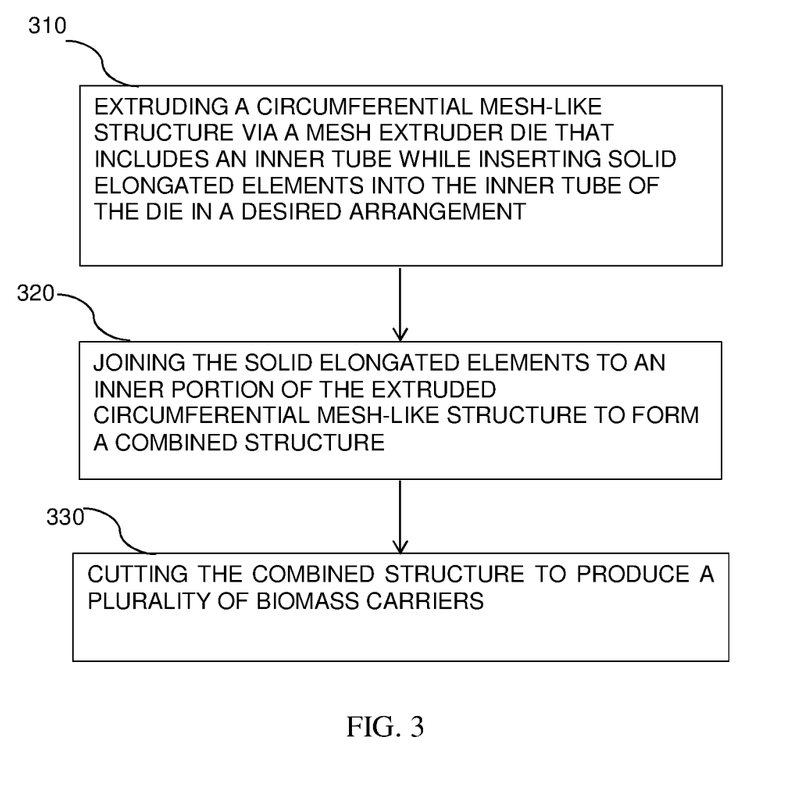
FIG. 3 is a flowchart of a method of making biomass carriers according to some embodiments of the invention.

Reference is made to FIG. 3, which illustrates a flowchart of method of making or producing biomass carriers according to some embodiments of the invention. In operation 310, the method may include extruding a circumferential mesh-like structure via a mesh extruder die that includes an inner tube while simultaneously inserting solid elongated elements into the inner tube of the die in a desired arrangement. An exemplary apparatus for manufacturing a biomass carrier according to the invention that includes a mesh extruder is illustrated and discussed with respect to FIG. 4.

A molten polymer may be introduced into a mesh extruder and may be led by a lead screw into a die designed to extrude mesh-like structures. The die may include a set of circumferential slits/slots for extruding a mesh. The die may include an inner tube for holding solid strips. The inner tube may have a diameter smaller than the diameter of the circumferential holes. The die may further include an outer tube having a diameter larger than the diameter of the circumferential holes, such that the inner tube (inner die) is located inside the outer tube (outer die) forming a space or a gap between the tubs. The molten polymer may be inserted by the lead screw into the space and may be injected from the space by the circumferential holes included in the die, to form the extruded circumferential mesh-like structure. In some embodiments, an active material (e.g., in the form of powder) may be added to the molten polymer to be mixed with the molten polymer in the extruder body, forming a composite material. Extruding circumferential mesh-like structure may include forming a mesh-like structure from the composite material.

The inner and outer dies may rotate relatively to each other and/or also vibrate vertically. The rotation of the die may define the vertical cords arrangement while the vertical vibration may define the outer rings. The relations between the vibration and rotation control the final mesh rings diameter. The final (cold/solid) mesh diameter exiting the die can be smaller or higher than the melted mesh diameter exiting the die.

The extruded circumferential mesh-like structure may have a thickness of less than 1000 micron, for example, in the range around, 100-500 or 50-150 micron. The polymer may be any polymer that may be extruded to form a mesh like structure, for example, a high density polyethylene (HDPE), a polyethylene terephthalate (PET), a low density polyethylene (LDPE) or a polypropylene (PP).

The elongated elements may be drawn via the inner tube, for example, towards the exit of the inner tube. The elongated elements may be held substantially parallel to the longitudinal axis of the die. The elongated elements may be arranged in a predetermined arrangement (e.g., arrangement 140) or may be arbitrarily located inside the inner tube. The solid elongated elements may include a polymer, for example HDPE, PET, LDPE or PP. The thickness of each elongated element may be less than 500 microns, for example, less than 250, microns, less than 150 microns, for example between 10-150 microns. The elongated elements may be pre-coated with a coating that includes an active component that enhances and encourage the growth of biomass.

The inner tube may be cooled to a temperature below the melting point or the solidification point of the polymer as to maintain the elongated elements in a solid state and to prevent major deformation of the elongated elements. The cooling may be required due to heat conducted from the extruder die head.

In operation 320, the method may include joining at least a portion of the solid elongated elements to an inner portion of the extruded circumferential mesh-like structure to form a combined structure. As the extruded circumferential mesh-like structure exits the die, simultaneously the elongated elements exit from the inner tube of the die, such that the elongated elements are encompassed by the extruded circumferential mesh-like structure. In some embodiments, the polymer included in the extruded circumferential mesh-like structure may be still in a liquid or semi-liquid state and may be easily joined to the portion of the solid elongated elements to form the combined structure. In another embodiment, the extruded circumferential mesh-like structure may be cooled to a solid state and may further be glued to the portion of the solid elongated elements, using any glue known in the art.

For example, the narrow side of at least some of the elongated elements may be welded or glued to the inner portion of the extruded circumferential mesh-like structure, as illustrated in FIGS. 1A and 2A. In some embodiments, some of the elongated elements may be welded or glued to other elongated elements in the desired arrangement, as illustrated in FIG. 1C, prior to the introduction of the elongated elements into the inner tube of the die. The outcome of the joining is an elongated combined structure.

Optionally, in operation 330, the method may include cutting the elongated combined structure to produce a plurality of biomass carrier having a desired length. The elongated combined structure may be cut, using any cutting apparatus known in the art. The length of the cut biomass carrier may be between 5 mm-50 mm. In some embodiments, following the cutting at least a portion of the carrier may be coated with a coating that includes an active component that enhances and encourage the growth of biomass. The carriers may be coated using any method known in the art, including spraying, spattering, immersing, gluing and others.

Reference is now made to FIG. 4, which illustrates an exemplary apparatus for manufacturing biomass carriers according to some embodiments of the invention. An apparatus 400 (e.g., a carrier production system) may include a horizontal extruder body 410, a vertical die 420, an elongated elements feeder 430, a support table 440 and combined structure support rollers 450. A combined structure 460 may be manufactured using apparatus 400 and then cut to biomass carriers (e.g., carriers 10 or 20 illustrated in FIGS. 1A and 1B).

Extruder body 410 may include a polymer inlet 412 for introducing molten or solid polymer into apparatus 400. In some embodiments, the polymer may be introduced in a solid state into inlet 412 and may further be melted inside extruder body 410. Extruder body 410 may further include a lead screw (not illustrated) for leading the polymer from the inlet into vertical die 420. Vertical die 420 may include an inner tube 422 (illustrated in a dashed line) and an outer tube 424. Inner tube 422 may be located inside outer tube 424 such that a gap or a space 426 may be formed between inner tube 422 and outer tube 424. Molten polymer may be introduced from extruder body 410 to space 426 in vertical die 420.

Die 420 may further include a set of circumferential holes, slots, recesses and/or slits (not illustrated) for extruding a mesh. The holes, slots recesses and/or slits may be located at one end of space 426 in die 420 (for example at the bottom). The circumferential holes/slots/slits may have a diameter (or other outer dimension such as diagonal) higher than the diameter of inner tube 422 and smaller than the diameter of outer tube 424. The molten polymer may be injected from circumferential holes/slots/slits of die 420 to form a mesh-like structure, for example, structures 12 and 22 illustrated in FIGS. 1B and 2B.

Elongated elements feeder 430 may feed a plurality of solid elongated elements 435 into inner tube 422 in die 420. Elongated elements 435 may be a plurality of solid polymer strips (e.g., ribbons, threads). Elongated elements 435 may be arranged in a predetermined desired arrangement (e.g., arrangement 14 illustrated in FIG. 1C) or may be arbitrarily grouped together. In some embodiments, at least some of the elongated elements may be joined (e.g., welded or glued) to other elongated elements, prior to feeding elongated elements 435 into feeder 430, as illustrated for example in FIG. 1C. Plurality of elongated elements 435 may be fed into inner tube 422 such that the elongated elements may be substantially parallel to the longitudinal axis of inner tube 422.

Inner tube 422 may be kept at temperature below the softening temperature (e.g., the melting point, glass transition point or the solidification point) of the polymer included in elongated elements 435, to maintain elongated elements 435 in a solid state inside die 420 and to prevent the heat from the molten polymer flowing in space 426 from melting or deforming elongated elements 435. Die 420 may include protective elements, such as for example a protective sleeve or a cooling sleeve (not illustrated) to cool inner tube 422. Inner tube 422 may be cooled using any cooling elements or methods known in the art. Alternatively, the protective element may serve as an isolating element preventing heat from melting or deforming elongated elements 435.

Elongated elements 435 may leave die 420 from an opening in inner tube 422 at the same time that the mesh-like injected extruded from the circumferential holes/slots/slits such that elongated elements 435 are positioned in a space confined by the circumferential mesh-like structure and at least some of elongated elements 435 are joined to an inner portion of the mesh-like structure, to form combined structure 460. At least a portion of some elongated elements 435 may be joined to inner portion of the mesh-like structure by welding when the mesh like structure is still in a molten or semi-molten state or by gluing when the mesh like structure is in a solid state.

Combined structure 460 may be introduced to a holding (and optionally cooling and/or drying) system located in support table 440. Support table 440 may support extruder body 410, vertical die 420, feeder 430 and combined structure support rollers 450. Combined structure 460 may be rolled, cooled and/or dried on combined structure support rollers 450. Leaving combined structure support rollers 450 combined structure 460 may be cut using any cutting device or method (not illustrated) to form biomass carriers according to some embodiments of the invention, for example, to form carriers 10 or 20.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A biomass carrier for use in a fluid treatment system, the biomass carrier comprising:
   an extruded circumferential mesh-like structure having a cylindrical shape; and
   elongated elements positioned in a space confined by the circumferential mesh-like structure, at least some of the elongated elements are joined to an inner portion of the mesh-like structure,
   wherein the biomass carrier is compressible.

2. The biomass carrier of claim 1, wherein the elongated elements are joined to the inner portion of the mesh-like structure during an extrusion process that forms the extruded circumferential mesh-like structure.

3. The biomass carrier of claim 1, wherein the biomass carrier is compressible along the elongated elements.

4. The biomass carrier of claim 1, wherein the circumferential mesh-like structure has a thickness of less than 1000 micron.

5. The biomass carrier of claim 1 comprising a polymeric material having a density of 0.8-1.2 gram/cm3.

6. The biomass carrier of claim 1, wherein the mesh-like structure comprises a rhombus mesh.

7. The biomass carrier of claim 1, wherein the extruded mesh-like structure comprises a plurality of threads arranged in the cylindrical shape parallel to the extruder's central axis and interconnected by at least two end-rings having equal radii.

8. The biomass carrier of claim 1, wherein the elongated elements have a width of 2.5-20 mm.

9. The biomass carrier of claim 1, wherein the biomass carrier comprises a polymeric material.

10. The biomass carrier of claim 9, wherein the polymeric material comprises a high density polyethylene (HDPE), a polyethylene terephthalate (PET), a low density polyethylene (LDPE), a polypropylene (PP) or a combination thereof.

11. The biomass carrier of claim 1, wherein the thickness of the extruded circumferential mesh-like structure is less than 500 micron.

12. The biomass carrier of claim 1, wherein the thickness of the elongated elements is less than 250 micron.

13. The biomass carrier of claim 1, wherein the biomass carrier has a compression ratio of at least 1:1.4.

14. The biomass carrier of claim 1, having a length of between 5 mm and 50 mm.

15. The biomass carrier of claim 1, further comprising an active coating on at least a portion of the biomass carrier.

16. The biomass carrier of claim 15, wherein the active coating comprises active carbon.

17. The biomass carrier of claim 1, further comprising an active coating on at least a portion of the elongated elements.

18. The biomass carrier of claim 1, wherein the extruded circumferential mesh-like structure comprises a reactive material.

19. The biomass carrier of claim 1, wherein the biomass carrier is manufactured by:
   feeding the elongated elements into a protective sleeve located inside an inner die during extrusion of the polymeric mesh-like structure, wherein the elongated elements comprises solid polymeric material;
   extruding the mesh-like structure from the die while directing the elongated elements to exit the die; and
   joining the elongated elements to an internal surface of the mesh-like structure.

20. The biomass carrier of claim 1, wherein the biomass carrier is configured to be compressed under an external force to at least below 70% of its original volume.

21. The biomass carrier of claim 1, wherein the elongated elements are arranged with axial symmetry within the circumferential mesh-like structure.

22. The biomass carrier of claim 1, wherein the circumferential cylindrical mesh-like structure has a constant radius.

23. A method of manufacturing a plurality of biomass carriers, comprising:
feeding solid elongated elements comprising polymeric material into a protective sleeve located inside an inner die during extrusion of a polymeric mesh-like structure;
extruding the mesh-like structure from the die while directing the elongated elements to exit the die;
affixing the elongated elements to an internal surface of the mesh-like structure, wherein the extruded mesh-like structure has a cylindrical shape and is circumferential to the elongated elements, and
cutting the mesh-like structure with the affixed elongated elements transversely to form the plurality of biomass carriers.

* * * * *